United States Patent
Nüsser et al.

(10) Patent No.: US 7,150,711 B2
(45) Date of Patent: Dec. 19, 2006

(54) METHOD FOR CONTROLLING AN ASSIST PUMP FOR FLUID DELIVERY SYSTEMS WITH PULSATILE PRESSURE

(75) Inventors: Peter Nüsser, Berlin (DE); Johannes Müller, Berlin (DE); Frank Deus, Berlin (DE); Peter Göttel, Berlin (DE); Jan Hoffmann, Berlin (DE); Kurt Graichen, Berlin (DE); Andreas Arndt, Berlin (DE); Tobias Merkel, Kleinmachnow (DE)

(73) Assignee: Berlin Heart AG, Berlin (DE)

( * ) Notice: Subject to any disclaimer, the term of this patent is extended or adjusted under 35 U.S.C. 154(b) by 0 days.

(21) Appl. No.: 10/344,384

(22) PCT Filed: Apr. 26, 2002

(86) PCT No.: PCT/EP02/04688

§ 371 (c)(1),
(2), (4) Date: Jun. 11, 2003

(87) PCT Pub. No.: WO02/088547

PCT Pub. Date: Nov. 7, 2002

(65) Prior Publication Data

US 2005/0019167 A1    Jan. 27, 2005

(30) Foreign Application Priority Data

Apr. 30, 2001 (DE) ................................. 101 23 139

(51) Int. Cl.
*A61M 1/12* (2006.01)
*F04B 17/03* (2006.01)
*F04B 49/08* (2006.01)

(52) U.S. Cl. ............................ 600/17; 417/19; 417/20; 417/43; 417/356

(58) Field of Classification Search ................. 417/19, 417/20, 23, 44.2, 44.3, 43, 356, 423.12; 604/151; 600/16, 17

See application file for complete search history.

(56) References Cited

U.S. PATENT DOCUMENTS

| 4,598,697 A | 7/1986 | Numazawa et al. |
| 4,782,817 A | 11/1988 | Singh et al. |
| 4,846,152 A | 7/1989 | Wampler et al. |
| 4,944,748 A | 7/1990 | Bramm et al. |
| 5,269,353 A * | 12/1993 | Nanaji et al. ............... 137/587 |

(Continued)

FOREIGN PATENT DOCUMENTS

DE      196 13 388      10/1996

(Continued)

*Primary Examiner*—Michael Koczo, Jr.
(74) *Attorney, Agent, or Firm*—Brinks Hofer Gilson & Lione

(57) ABSTRACT

Method for controlling an assist pump for fluid delivery systems with pulsatile pressure. If for example a heart assist pump is driven with a constant number of revolutions, it is achieved, that the blood is also delivered through the assist pump, even when the heart chamber is in the decontraction phase. With the present method it is achieved, that an assist pump only acts supportingly in the pressure phase of the main pump, in such a way, that the pressure difference between the input side and the output side of the assist pump is continuously determined and the number of revolutions of the assist pump is controlled in such a way, that the determined pressure difference does not fall below a predetermined value and the rate of flow does not sink below zero.

12 Claims, 5 Drawing Sheets

U.S. PATENT DOCUMENTS

| | | | |
|---|---|---|---|
| 5,868,133 A * | 2/1999 | DeVries et al. | 128/204.21 |
| 6,129,660 A | 10/2000 | Akamatsu et al. | |
| 6,161,772 A * | 12/2000 | Anfindsen | 239/71 |
| 6,443,983 B1 * | 9/2002 | Nagyszalanczy et al. | 600/17 |
| 6,464,464 B1 * | 10/2002 | Sabini et al. | 417/19 |
| 6,572,530 B1 * | 6/2003 | Araki et al. | 600/17 |
| 6,623,420 B1 * | 9/2003 | Reich et al. | 600/17 |
| 6,808,508 B1 * | 10/2004 | Zafirelis et al. | 604/131 |
| 2002/0173695 A1 * | 11/2002 | Skliar et al. | 600/16 |
| 2002/0183585 A1 * | 12/2002 | Willems et al. | 600/17 |
| 2003/0139643 A1 * | 7/2003 | Smith et al. | 600/16 |
| 2004/0152944 A1 * | 8/2004 | Medvedev et al. | 600/17 |

FOREIGN PATENT DOCUMENTS

| | | |
|---|---|---|
| DE | 199 19 625 | 11/2000 |
| EP | 1 070 511 | 1/2001 |
| WO | WO 00/64030 | 10/2000 |

* cited by examiner

METHOD FOR CONTROLLING AN ASSIST PUMP FOR FLUID DELIVERY SYSTEMS WITH PULSATILE PRESSURE

BACKGROUND OF THE INVENTION

The invention relates to a method for controlling an assist pump (a support pump) for fluid delivery systems with pulsatile pressure.

It is known, to arrange further pumps for the assistance of pulsatile working pumps in a fluid delivery system. Such assist pumps are normally driven at a constant number of revolutions. In correspondence to the differential pressure/volume flow—characteristic line of the assist pump, the assist pump reacts, when the input pressure is increased and the resulting change of the delivery height (difference of the input pressure to the output pressure), with an increase of the volume flow and vice versa. The volume flow through the assist pump falls, however, also in the low pressure phase, i.e. at a reduced input pressure, not to zero.

The steeper the differential pressure/volume flow—characteristic line of the pump is, the higher is the remaining volume flow in this phase. This can lead to the fact, that the volume flow stops and that the delivery system arranged in front of the assist pump, including the main pump, are acted upon by a negative pressure, which can lead to different disadvantages. E.g. the still flowing fluid can experience high turbulences, when flowing into the pump chamber of the main pump.

An especially sensitive fluid delivery system is the blood flow. Blood circulates, driven by rhythmical contraction of the heart, in a closed vascular system. During an error of the function of the heart, in the last few years blood flow assist pumps have been used, which should support a still present pulse of the heart. The blood is guided from the left heart chamber by means of bypassing the heart valve into the assist pump and from there into the aorta. Such assist pumps can be designed according to the displacement principal as pulsatile pumps and also according to the turbo principal as radial or axial flow machines. Pulsatile pumps according to the displacement principal have shown not to be advantageous because of the necessary expenditure for the synchronisation with the heart beat. In the pumps, working according to the turbo principal, the axial pumps are preferred, because of their small dimensions.

The known axial blood pumps consist essentially of an outer cylindrical tube, in which a delivery element, which is formed as a rotor of a motor stator arranged at the outside, rotates and moves the blood in axial direction. Furthermore, it is known, to magnetically support the rotor free of contact. Such an assist pump is known from WO 00/640 30.

If such an assist pump is driven with a constant number of revolutions, it results because of the above described conditions, that the blood is still delivered by the assist pump, when the heart chamber is in the decontraction phase.

The invention has the object to provide a method, by which the volume flow in an assist pump only acts supportingly in a simple way in the pressure phase of the main pump.

BRIEF SUMMARY OR THE INVENTION

The object is solved according to the invention by the features of claim 1. Suitable embodiments are subject of the dependent claims.

According to this the pressure difference between the input side and the output side of the assist pump as well as the rate of flow through the assist pump are constantly determined. The number of revolutions of the assist pump is controlled in such a way, that the determined pressure difference does not fall below a predetermined value and the rate of flow does not fall below zero.

According to one preferred embodiment of the method as an assist pump an axial pump, having an electronically commutated synchronous motor and a permanently magnetic support and control coils for the magnetic support control of the rotor, is used and the pressure difference between the input side and the output side of the assist pump is determined, such, that from the control current of the control coils and the actual rotor position, which are present as values of the support control, the interference force, proportional to the pressure difference, onto the rotor is determined. At the same time the rate of flow through the assist pump can be determined by means of the actual number of revolutions and the pressure difference from the predetermined differential pressure/volume flow—characteristic field of the assist pump. In this way, no separate sensors are necessary for the pressure and the rate of flow.

BRIEF DESCRIPTION OF THE DRAWINGS

The invention is described in detail in the following by means of a blood flow assist pump as an embodiment for the method. In the drawings.

DETAILED DESCRIPTION OF THE INVENTION

Figure 1:
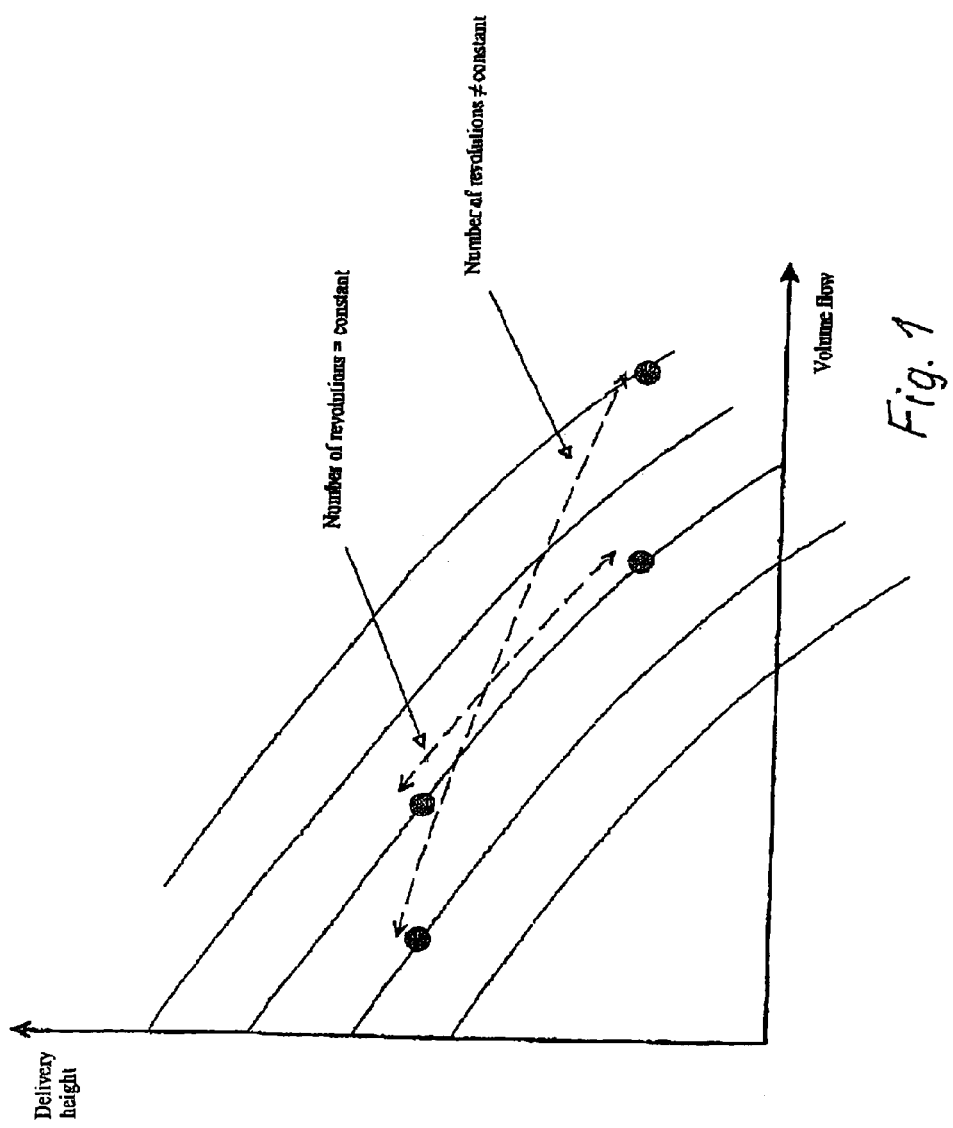
FIG. 1 shows a characteristic field of an axial pump.

FIG. 1 shows a characteristic field of a blood pump with axial flow. The characteristic lines show, respectively, the dependency of the sudden change of pressure of the pump (delivery height) of the delivered volume per time unit at a specific number of revolutions. During the operation with a constant number of revolutions the working point of the pump moves also along a characteristic line.

The extent of the flow change during a given pressure difference change depends on the steepness of the characteristic line. To change this value visibly, the number of revolutions of the pump has to be changed in dependency of the instantaneous delivery height. The working point moves, now, not anymore along a line of constant number of revolutions, but wanders between lines of different numbers of revolutions. The number of revolutions is, for this, the to be influenced parameter. If a predetermined increase of the delivery height should cause a higher decrease of the flow, than, predetermined by the natural pump characteristic line, the number of revolutions of the rotor has to be reduced with increasing delivery height and has to be increased with decreasing delivery height. From this a wandering in the characteristic field and, therefore, a visible reduction of the steepness of the characteristic line of the pump is achieved.

For a natural blood flow system the condition, that the blood should not again flow back to the heart during the diastolic phase, is valid. In an intact blood flow system the heart valve carries out this function. Therefore, the blood pump also has to imitate the function of the heart valve. For the control according to the invention, therefore, the delivery height and the volume flow have to be known. These can be determined by means of a suitable sensory mechanism. They, however, can also be determined by skilled selection of a specific pump type from the control data of the pump drive.

Figure 2:
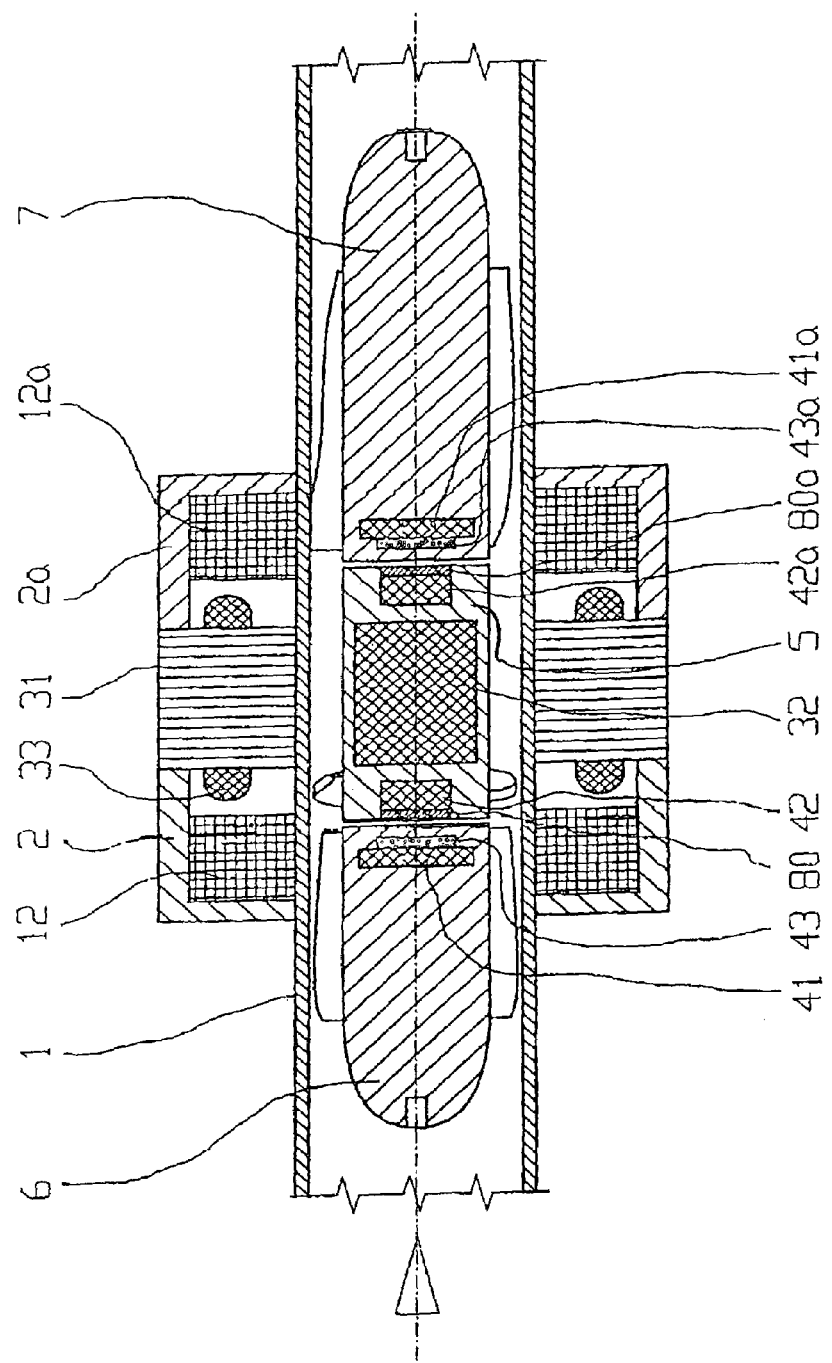
FIG. 2 shows a heart assist pump suitable for the implementation of the method.

FIG. 2 shows such an axial blood assist pump suitable for the implementation of the method. The drive of the blood assist pump works according to the principal of an electronically commutated synchronous motor. The motor has a stator, comprising a metal sheet packet 31, windings 33 and iron flux return hoods 2, 2a and a rotor 5 with permanent magnetic core 32. The stator encloses a tubular hollow body 1, in which in the axial direction a fluid, in the present case blood, is delivered. The rotor 5 is support magnetically and free of contact.

The magnetic support consists of permanent magnets 42, 42a at the rotor end sides and permanent magnets 41, 41a at the end sides of the guiding devices 6 and 7. The guiding devices 6, 7 are mounted on the inner wall of the tubular hollow body 1.

To the magnetic support, furthermore, control coils 12, 12a belong. Sensor coils 43, 43a in the guiding devices 6, 7 and short circuit rings 80, 80a opposed thereto serve for measuring the actual rotor position.

The pairs of permanent magnets 41, 42; 41a, 42a are, respectively, attracting each other. The pairs are magnetically arranged in series.

Without an additional stabilisation the rotor 5 would be attracted to one side, in axial direction an instable equilibrium is present. In radial direction both pairs of magnets act in a centering manner, the radial position is, therefore, passively stable.

The control coils 12, 12a are electrically connected in series and are arranged magnetically in such a way, that a current weakens the magnetic field of one of the pairs of magnets and increases the magnetic field of the other pair. The magnetic flux return path is achieved via the iron flux return hoods 2, 2a and the metal sheet packet 31 of the stator.

The axial position of the rotor 5 can be determined by means of the sensor coils 43, 43a. The sensor coils 43, 43a are acted upon by a higher frequent voltage. During the axial movement of the rotor 5 a mutual detuning of the sensor coils 43, 43a is achieved. By means of the arrangement of the sensor coils 43, 43a in a bridge connection a measuring signal for the axial position of the rotor 5 can be determined.

The axial stabilisation is achieved via a control circuit. The measured rotor position is the input signal of the controller. Its output signal, the adjustment current, is delivered into the control coils 12, 12a. In this way, the position of the rotor 5 between the two end abutments can be controlled. This controlling is then switched currentless, when the sum of all the magnetic and mechanical forces is zero. In an unloaded motor, this is the case in the mean position. Thus, the control current is practically infinitively small. When the rotor 5 is axially loaded, it has to be moved against the acting force, till the then asymmetrical forces of the permanent magnets 41, 42; 41a, 42a compensate the interference force. At this point the control current is again infinitively small.

The controller is formed as a PID-controller with an $I_2$-portion for the zero current control. The controller can control sudden (jump-like) interferences nearly without overshooting. The zero point search is quick enough, to hold the control current uptake near zero during the application specific interference frequency.

The measuring signal is determined from a bridge connection of the sensor coils 43, 43a. The measuring is, however, made difficult by the control of the current of the control coils and of the current of the motor. Because of this, with a tuning-out method, measurements are only carried out during interference-free time intervals between the switching impulses. During the switching impulse duration the last measured value before the tuning-out is stored.

The axial stabilisation of the magnetically supported rotor 5 allows an estimation of the interference force acting on the rotor 5. The sum of the forces acting on the rotor 5 has to be zero at every point in time. The forces of the permanent magnet system, the forces of the electromagnet systems and the mechanical forces, especially pressure forces, as well as frictional forces, dampening forces and acceleration forces, have to balance each other out. Under the precondition, that the frequencies of the to be determined interference forces are low in comparison with the border frequency of the stabilisation control circuits, the dampening and acceleration forces can be neglected. Therefore, the interference forces are determined in such:

interference force=control current×electrical sensitivity−rotor position×axial stiffness.

The electromagnetic sensitivity is a constant depending on the magnetic circuit. The axial stiffness is an expression of the force, which is necessary, to displace the rotor 5 axially by a specific amount and is also constant in the range being of interest here (rotor gap around 0.5 to 2.5 mm).

By means of the interference force a value for the proportional pressure jump of the assist pump is available, which can be used as a dynamic signal for the control of the number of revolutions. At the same time the volume flow can be determined by means of the pressure difference and the number of revolutions of the pump with known pump characteristic line.

By means of the selection of a special blood pump and the skillful processing of the data known of the rotor support control it can be achieved in this way, that the use of sensors for the pressure and the rate of flow can be fully eliminated.

The here shown blood pump is also especially suitable because of other reasons for the control according to the invention. The synchronous motor, commutated without sensors, allows a high angle acceleration of the pump rotor. This acceleration and the therewith connected axial and radial forces onto the rotor 5 are tolerated by the magnetic support. The usable range of the numbers of revolutions is not limited by the resonance frequencies of the radial rotor suspension. Resonances remain always dampened. Because of this a variation of the number of revolutions starting from the minimal number of revolutions up to the maximal number of revolutions is possible in a time of around 50 ms. Between the time function of the number of revolutions of the rotor and of the pump flow no delay times are visible.

Figure 3:
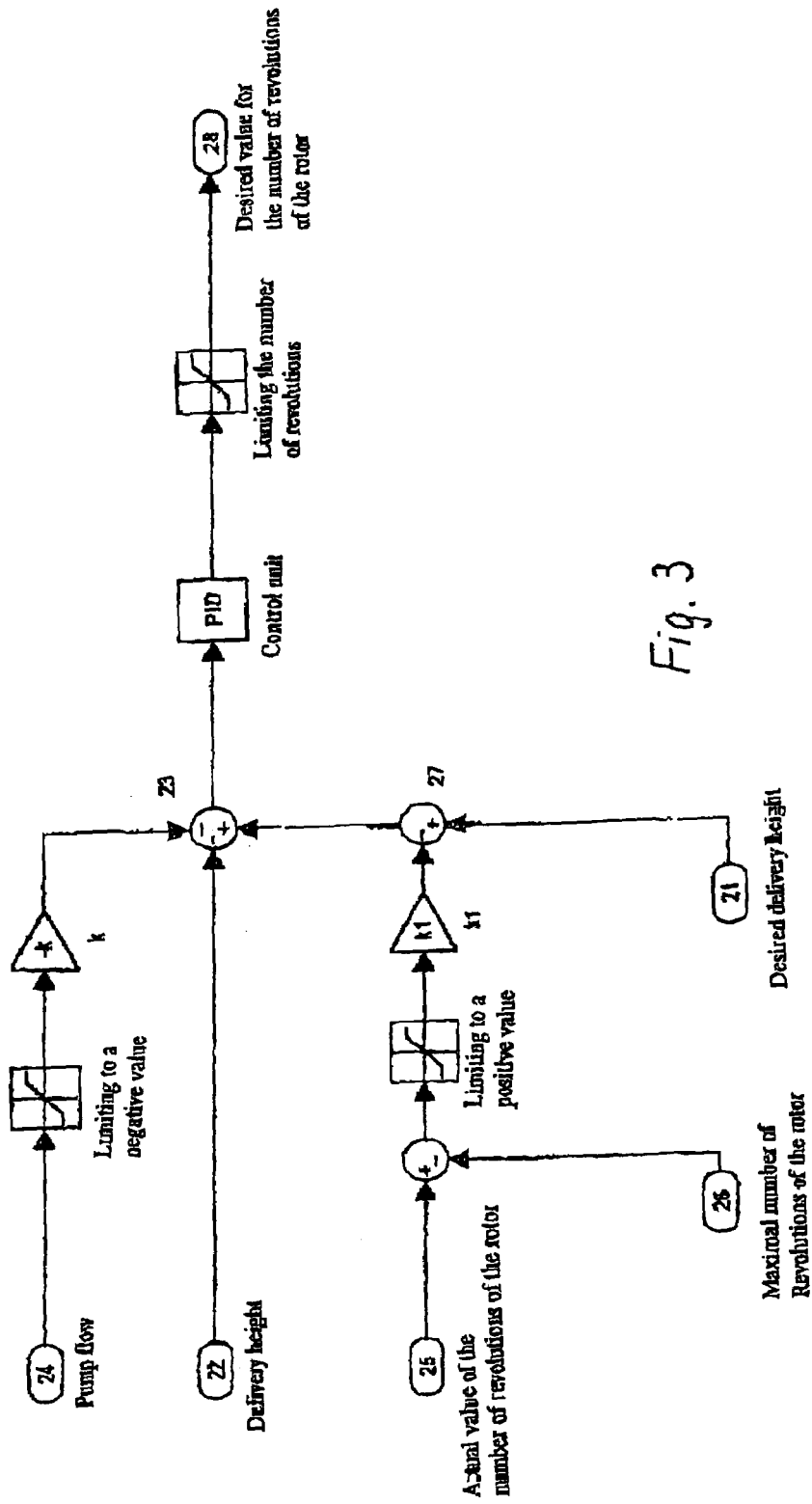
FIG. 3 shows a block diagram of an example for the control according to the invention.

FIG. 3 shows an example for a possible control circuit for the control of the number of revolutions. The desired delivery height of the assist pump is input into pressure head 21. It depends on, which natural pressure can still be produced by the heart and how much additional pressure according to this the assist pump has to produce. The as described above determined pressure difference between the input side and the output side of the assist pump is input as the necessary delivery height at the branch 22 for a desired—actual-comparison in a comparator 23. From this, the control deviation results, which is adjusted by a PID-controller with following limiter for the adjustment value of the number of revolutions. This adjustment value is turned into a corresponding number of revolutions by the control of the motor. Numeral 28 indicates the desired set point for the number of revolutions per minute by the rotor.

Figure 4:
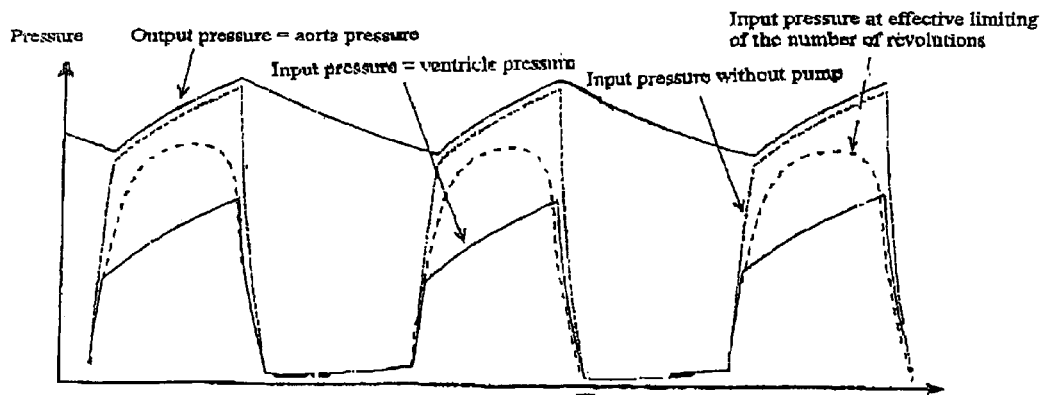
FIG. 4 shows the pressure-time graph at the heart assist pump.
Figure 5:
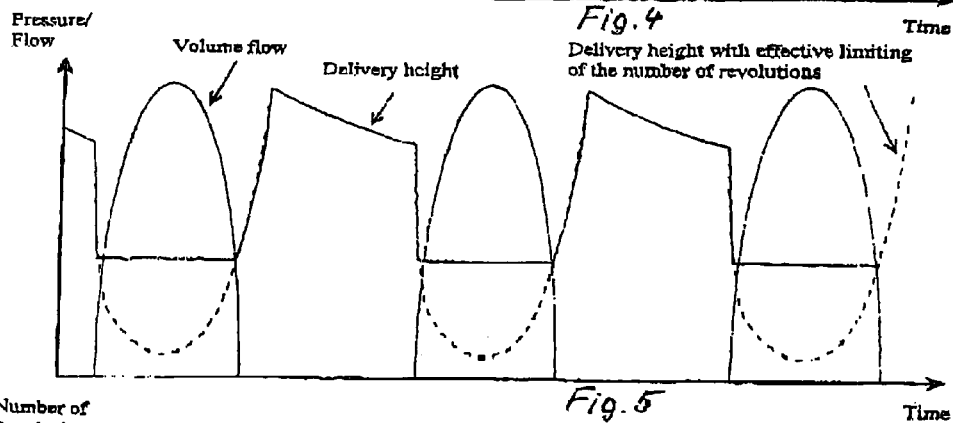
FIG. 5 shows the march of the delivery height and of the volume flow at the heart assist pump.
Figure 6:
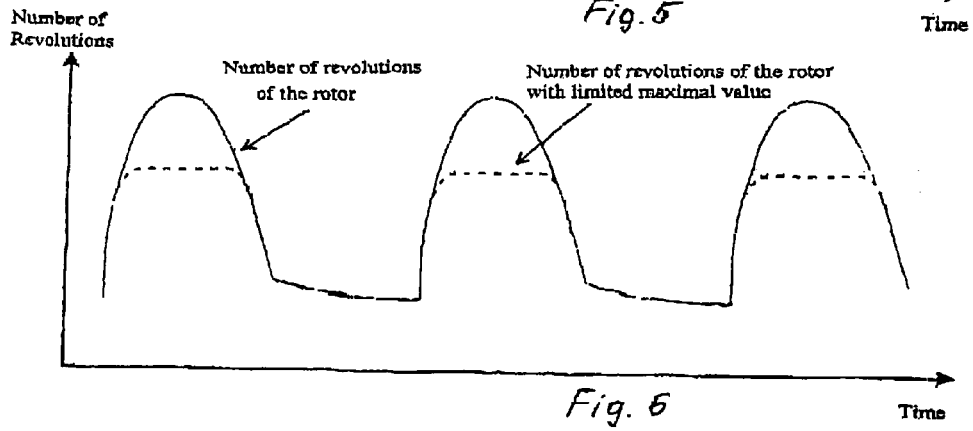
FIG. 6 shows the march of the number of revolutions of the heart assist pump.

FIGS. 4 to 6 show the march of time of the characteristic data in the systolic and diastolic phase. The assist pump is arranged between an expulsion from the left heart chamber (ventricle) and the aorta. The ventricle pressure of the heart forms the input pressure of the assist pump, the aorta pressure through the assist pump is at the same time its output pressure.

The pressure difference between the natural pressure of the ventricles and the desired aorta pressure has to be produced in the systolic phase by the assist pump. In the diastolic phase only a return flow of the blood into the heart chamber should be prevented.

FIG. 5 shows the delivery height of the assist pump given by these conditions. The desired value of the delivery height corresponds roughly to the half mean aorta pressure. If pressure falls below this desired value, the control of the number of revolutions starts, the pump then accelerates, if necessary up to the maximal number of revolutions, and delivers the blood into the aorta. If the delivery height increases again during decreasing pressure of the ventricle, the adjustment value of the number of revolutions and therewith, the number of revolutions of the rotor falls till the diastolic phase is reached.

By means of introducing only the negative values to the volume flow at branch 24, i.e. a possible back flow to the ventricle, via a control amplifier k onto the comparator 23 it is ensured, that in the diastolic phase such a number of revolutions is maintained, that the volume flow does not fall below zero, but is kept on a value near zero.

In the present embodiment the desired delivery height is, furthermore, influenced by a correction value, which is determined by the comparison of the actual number of revolutions of the rotor with a maximal number of revolutions of the rotor. If the number of revolutions of the rotor, existent at the branch 25, exceeds a predetermined maximal number of revolutions of the rotor at the branch 26, the deviation, is delivered, amplified via a control amplifier k1, with negative sign to a comparator 27, at which the desired delivery height is applied. The to be controlled desired—actual-deviation of the delivery height is, therefore, in advance limited, when reaching a maximal number of revolutions of the rotor.

Figure 8:
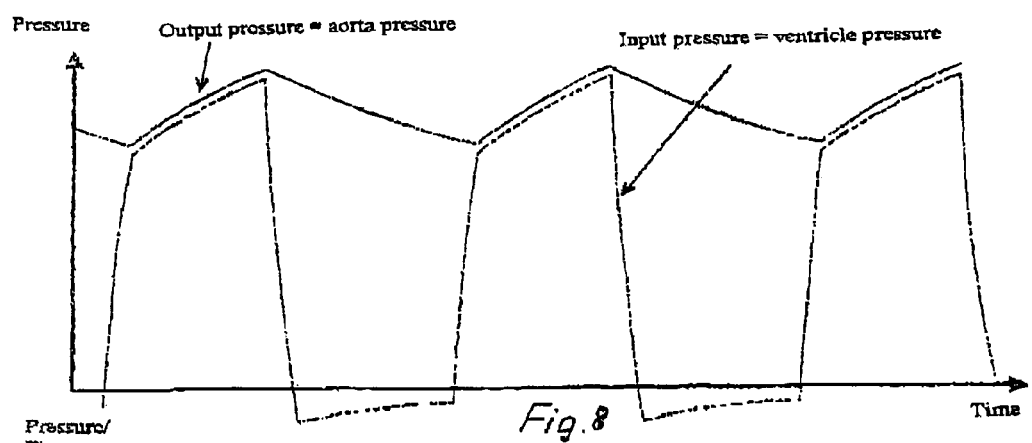
FIG. 7 shows in contrast the march of the delivery height and of the volume flow and FIG. 8 shows the pressure-time graph at a heart assist pump driven at a constant number of revolutions.
Figure 7:
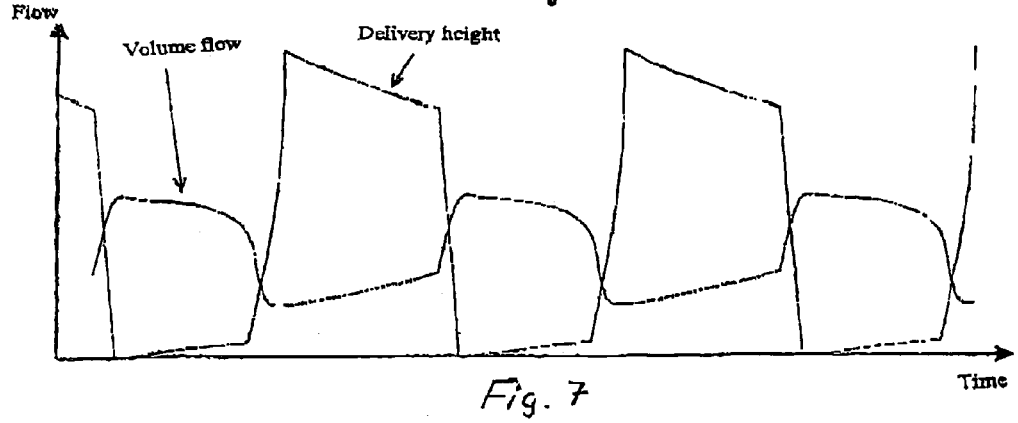

FIG. 7 shows a pressure/volume-time graph and FIG. 8 shows the pressure-time graph at the ventricle during the operation of a pump with a constant number of revolutions. It is apparent that the pump in the diastolic phase draws and pumps empty the heart chamber. The desired pressure relief of the heart is not achieved.

With the method shown in this embodiment not only sensory mechanisms disturbing and causing additional expenditure can be eliminated, but also a pulsatile volume flow present in a fluid delivery system can be supported, without having to distinguish by means for the synchronisation, between the two operational conditions.

The invention claimed is:

1. A method for controlling an assist pump for fluid delivery systems with pulsatile pressure, comprising the steps of
   continuously determining the pressure difference between the input side and the output side of the assist pump as well as the rate of flow through the assist pump and
   controlling the number of revolutions per minute of the assist pump by increasing the number of revolutions per minute during the systole so that the determined pressure difference does not fall below a predetermined value and by decreasing the number of revolutions per minute during the diastole so that the rate of flow does not fall below zero.

2. The method according to claim 1,
   wherein the assist pump is an axial flow pump with electronically commutated synchronous motor and permanent magnetical support and control coils for the magnetical position control of the rotor and
   wherein the pressure difference between the input side and the output side of the assist pump is determined in such a way, that from the control current of the control coils and the actual rotor position, which are present as values of the position control, the interference force onto the rotor, which is proportional to the pressure difference, is determined.

3. The method according to claim 1,
   wherein the flow rate through the assist pump is determined by the actual number of revolutions per minute and the pressure difference from a beforehand measured differential pressure/volume flow—characteristic field of the assist pump.

4. The method according to claim 1,
   wherein the number of revolutions per minute of the assist pump is limited to a predetermined maximal value.

5. The method according to claim 1,
   further comprising using a PID-controller for controlling the number of revolutions per minute.

6. The method according to claim 1,
   further comprising adding a correction value, determined from a comparison from the number of revolutions per minute of the rotor and a predetermined maximal value of the number of revolutions per minute of the rotor, to the pressure difference-desired value.

7. A method for controlling an assist pump for fluid delivery systems with pulsatile pressure, comprising the steps of
   continuously determining the pressure difference between the input side and the output side of the assist pump as well as the rate of flow through the assist pump,
   adding a correction value, determined from a comparison from the number of revolutions per minute of the rotor and a predetermined maximal value of the number of revolutions per minute of the rotor, to the pressure difference-desired value, and
   controlling the number of revolutions per minute of the assist pump in such a way, that the determined pressure difference does not fall below a predetermined value and the rate of flow does not fall below zero.

8. The method according to claim 7,
   wherein the flaw rate through the assist pump is determined by the actual number of revolutions per minute and the pressure difference from a beforehand measured differential pressure/volume flow—characteristic field of the assist pump.

9. The method according to claim 7,
   wherein the number of revolutions per minute of the assist pump is limited to a predetermined maximal value.

10. A method for controlling an assist pump for fluid delivery systems with pulsatile pressure, wherein the assist pump is an axial flow pump with electronically commutated synchronous motor and permanent magnetical support and control coils for the magnetical position control of the rotor, the method comprising the steps of continuously determining the pressure difference between the input side and the output side of the assist pump from the control current of the control coils and the actual rotor position, which are present as values of the position control, the interference force onto the rotor which is proportional to the pressure difference, as well as the rate of flow through the assist pump and controlling the number of revolutions per minute of the assist pump in such a way, that the determined pressure difference does not fall below a predetermined value and the rate of flow does not fall below zero.

11. The method according to claim 10, further comprising using a PID-controller for controlling the number of revolutions per minute.

12. The method according to claim 10, further comprising adding a correction value, determined from a comparison from the number of revolutions per minute of the rotor and a predetermined maximal value of the number of revolutions per minute of the rotor, to the pressure difference-desired value.

* * * * *

UNITED STATES PATENT AND TRADEMARK OFFICE
CERTIFICATE OF CORRECTION

PATENT NO.        : 7,150,711 B2
APPLICATION NO. : 10/344384
DATED             : December 19, 2006
INVENTOR(S)       : Peter Nüsser et al.

It is certified that error appears in the above-identified patent and that said Letters Patent is hereby corrected as shown below:

Column 6
Line 57, delete "flaw" and insert --flow--.

Signed and Sealed this

Sixth Day of March, 2007

JON W. DUDAS
*Director of the United States Patent and Trademark Office*